(12) United States Patent
Goodson et al.

(10) Patent No.: US 8,021,148 B2
(45) Date of Patent: Sep. 20, 2011

(54) INTRAORAL LIGHT-EMITTING DEVICE

(75) Inventors: J Max Goodson, Cambridge, MA (US); Nikos Soukos, Saugus, MA (US)

(73) Assignee: Forsyth Dental Infirmary for Children, Cambridge, MA (US)

( * ) Notice: Subject to any disclaimer, the term of this patent is extended or adjusted under 35 U.S.C. 154(b) by 33 days.

(21) Appl. No.: 11/743,816

(22) Filed: May 3, 2007

(65) Prior Publication Data

US 2007/0259310 A1  Nov. 8, 2007

Related U.S. Application Data

(60) Provisional application No. 60/797,024, filed on May 3, 2006.

(51) Int. Cl.
*A61C 3/00* (2006.01)

(52) U.S. Cl. .......................................................... 433/29

(58) Field of Classification Search .................... 433/29, 433/37; 362/572–573, 804
See application file for complete search history.

(56) References Cited

U.S. PATENT DOCUMENTS

| | | | |
|---|---|---|---|
| 5,079,262 A | 1/1992 | Kennedy et al. | |
| 5,211,938 A | 5/1993 | Kennedy et al. | |
| 5,234,940 A | 8/1993 | Kennedy et al. | |
| 5,422,093 A | 6/1995 | Kennedy et al. | |
| 6,026,828 A | 2/2000 | Altshuler | |
| 6,077,073 A | 6/2000 | Jacob | |
| 6,162,055 A | 12/2000 | Montgomery et al. | |
| 6,202,242 B1 | 3/2001 | Salmon et al. | |
| 6,343,933 B1 | 2/2002 | Montgomery et al. | |
| 6,416,319 B1 | 7/2002 | Cipolla | |
| 6,514,075 B1 | 2/2003 | Jacob | |
| 6,623,272 B2 | 9/2003 | Clemans | |
| 6,954,961 B2 | 10/2005 | Ferber et al. | |
| 2004/0043349 A1* | 3/2004 | Liao ................................ 433/29 |
| 2005/0221251 A1* | 10/2005 | Soukos et al. ................... 433/29 |
| 2005/0239018 A1* | 10/2005 | Green et al. .................... 433/140 |
| 2006/0085052 A1* | 4/2006 | Feuerstein et al. ............. 607/90 |
| 2006/0127837 A1* | 6/2006 | Nguyen et al. .................. 433/29 |
| 2006/0240375 A1 | 10/2006 | Soukos et al. | |

FOREIGN PATENT DOCUMENTS

WO   WO 2004/084752   10/2004

OTHER PUBLICATIONS

Soukos, N. S. et al. "Phototargeting oral black-pigmented bacteria." Antimicrob. Agents Chemother. 49:1391-1396 (2005).

* cited by examiner

*Primary Examiner* — Todd Manahan
*Assistant Examiner* — Matthew Nelson
(74) *Attorney, Agent, or Firm* — Antoinette G. Giugliano, PC; AGG Intellectual Property Law

(57) ABSTRACT

The present invention relates to methods, systems, kits and devices that emit light to the oral cavity. The device includes a light source; a power source in electrical communication with the light source; and a bite actuated switch in electrical communication with the power source and the light source. The device is a size or shape that fits within an oral cavity of an individual. Since the device along with the light and power source are self contained, the user have their hands-free and can perform other activities while using the device. The device, methods, systems, and kits, further include the use of an agent (e.g., antibacterial agents, tooth whitening agents, cleaning agents) that assists or enhances the efficacy of the light therapy.

13 Claims, 7 Drawing Sheets

INTRAORAL LIGHT-EMITTING DEVICE

RELATED APPLICATION

This application claims the benefit of U.S. Provisional Application No. 60/797,024, filed May 3, 2006, entitled "Intraoral Light-emitting Device for Treatment of Oral Diseases" by J. Max Goodson and Nikos Soukos.

The entire teachings of the above application are incorporated herein by reference.

BACKGROUND OF THE INVENTION

Light has been used to treat certain oral diseases and conditions. Intraoral light emitting devices often obtain their power through wires attached to alternating current. Intraoral light emitting devices can also obtain their power through a battery pack placed outside the mouth or within the body of a handle that protrudes from the mouth. Devices with power wires prevent the user from moving freely around or from doing other things. Also, devices with battery packs in the handles need to be held in place by the user which ties up their hand. As such, these devices often prevent users for engaging in other activities during treatment with the device (e.g., brushing their hair, putting on make-up, shaving).

Additionally, certain safety concerns exists for some intraoral light emitting devices. In particular, such devices can be turned on by the user when the device is outside of the oral cavity and cause inadvertent exposure to the eye.

Accordingly, a need exists for a device that allows an individual to use an intraoral light emitting device hands-free and without being tethered to an electrical outlet so that the user can engage in other activities. A further need exists for a device that encourages activation during use, and not prior to or after use to avoid inadvertent eye exposure.

SUMMARY OF THE INVENTION

The present invention relates to oral light emitting devices having a light source; a power source in electrical communication with the light source; and a bite actuated switch in electrical communication with the power source and the light source. The device has a size and/or shape that fits within an oral cavity of an individual. In an embodiment, the size of the device has a width ranging between about 1½ inches to about 3½ inches (e.g., preferably between about 2 and 2½ inches), a depth ranging between about 1 inch to about 2 inches (e.g., preferably about 1½ inches), and a height ranging between about ½ inch to about 1½ inches (e.g., preferably about 1 inch). In one aspect, the power source and switch are encapsulated within the device, and the light source is either encapsulated within the device or disposed on the device. In another aspect, the device encapsulates the power source which, when in use, the power source resides within an oral cavity of an individual. The present invention further embodies a bitewing that houses the bite actuated switch. The device also includes housing that is liquid proof or waterproof. The device has a light source that emits a wavelength that ranges from about 350 nm to about 700 nm, a power density that ranges from about 1 mW/cm$^2$ to about 1000 mW/cm$^2$, an energy fluence that ranges from about 0.1 Joules/cm$^2$ to about 1000 Joules/cm$^2$, or any combination thereof. Another embodiment of the present invention includes a light source that is positioned to emit light to a portion of the tongue, teeth, gums, or to one or more lingual surfaces, buccal surfaces, palatal surfaces, or facial surfaces, or any combination thereof. In an embodiment, the device further comprises a compartment for housing or storing an agent that enhances the desired effect of the intraoral device. Optionally, the device includes a timer.

The present invention relates to methods for providing light to an oral cavity of a user. Methods for improving oral health, reducing the number of one or more bacteria, reducing symptoms associated with halitosis or one or more gum conditions or diseases are encompassed by the present invention. The steps of the methods include actuating a bite actuated switch, wherein, when actuated, the device emits light to the oral cavity. In another embodiment, the methods include inserting the device of the present invention into the oral cavity, and biting down on the device to actuate the switch to emit light to a surface of the oral cavity. When these steps are carried out, a reduction in one or more of the following occurs: a reduction in the number of one or more bacteria; a reduction in one or more symptoms associated with halitosis; and a reduction in one or more symptoms associated with one or more gum conditions or diseases. The steps further include administering or applying one or more agents for improving oral health or an agent that assists in eliminating bacteria, whitening teeth, improving halitosis, cleaning teeth, tongue or gums, or any combination thereof. Examples of such agents are chlorine dioxide, chlorhexidine, triclosin, oxidizing agents, photosensitizers, calcium and/or iron chelators and cleaning agents.

Additionally, methods for whitening teeth with the light emitting device described herein are included in the present invention. The methods involve applying or administering at least one tooth whitening agent; inserting the device into the user's oral cavity; and biting down on the bite actuated switch, wherein when actuated, the device emits light to one or more tooth surfaces of the oral cavity. The steps result in the whitening of one or more teeth.

The present invention pertains to oral light emitting systems or kits that includes the oral light emitting device. The device has a light source; a housing for a power source in electrical connection with the light source; and a bite actuated switch in electrical connection with the power source and the light source. The device has a size or shape that fits within an oral cavity of an individual. The system or kit further includes a power source (e.g., a battery such as a rechargeable battery), and/or an agent that assists in eliminating bacteria, whitening teeth, improving halitosis, cleaning teeth, tongue or gums, or any combination thereof.

The present invention has numerous advantages. The device of the present invention is designed to fit within the oral cavity and has no external tethered connection. The design further allows the user to activate it by biting down, and so the user has their hand free to do other things while utilizing the device. Also, since the light source turns on when the mouth is closed, the device of the present invention increases the safety of oral cavity light exposure by reducing inadvertent exposure to the eyes. The present invention allows for exposure to light that can be repeated at regular intervals as an adjunct to treatment of oral disease, which in turn, generally provides for better clinical outcomes.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

The present invention relates to a self-contained breath freshening device that fits in a user's mouth and is activated by biting down on the device. Upon activation, the device emits light at a wavelength, and power density to reduce one or more bacteria that causes bad breath (e.g., halitosis) and gum disease, to whiten teeth, and/or to improve an individuals overall oral health. As described herein, the device can be used together with oral agents (e.g., an oxidizing agent) to enhance the use of the device, as further described herein.

Figure 1A:
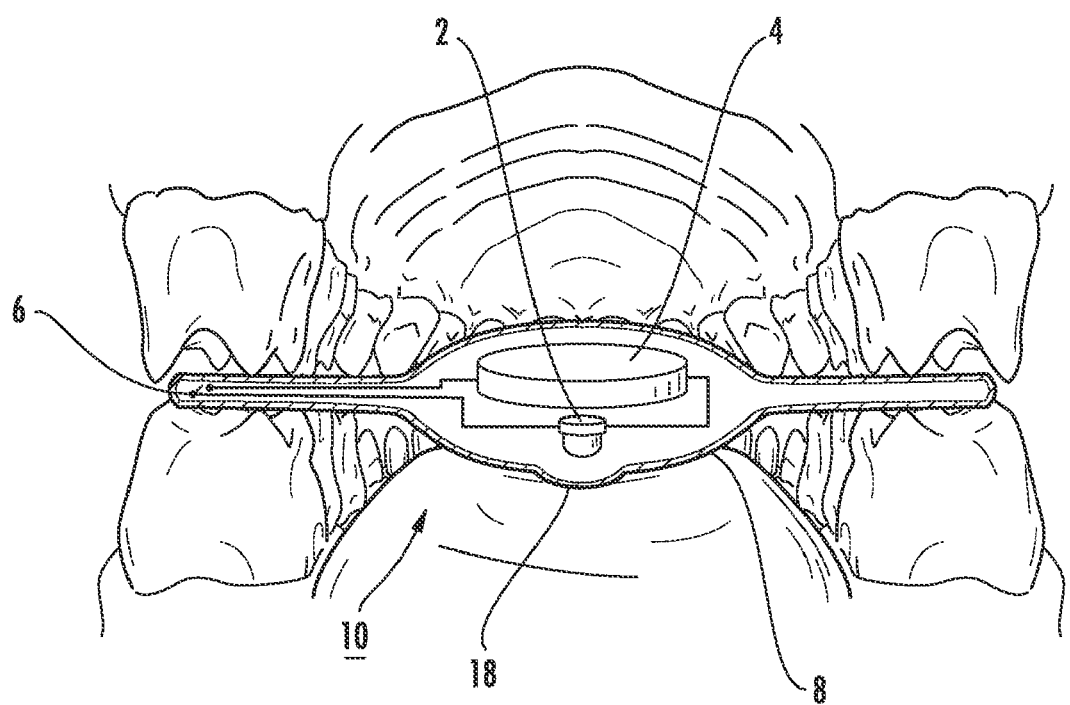
FIG. 1A is a drawing of a side view of an embodiment of the light emitting device of the present invention positioned in an oral cavity, wherein the device emits light to the tongue.
Figure 1B:
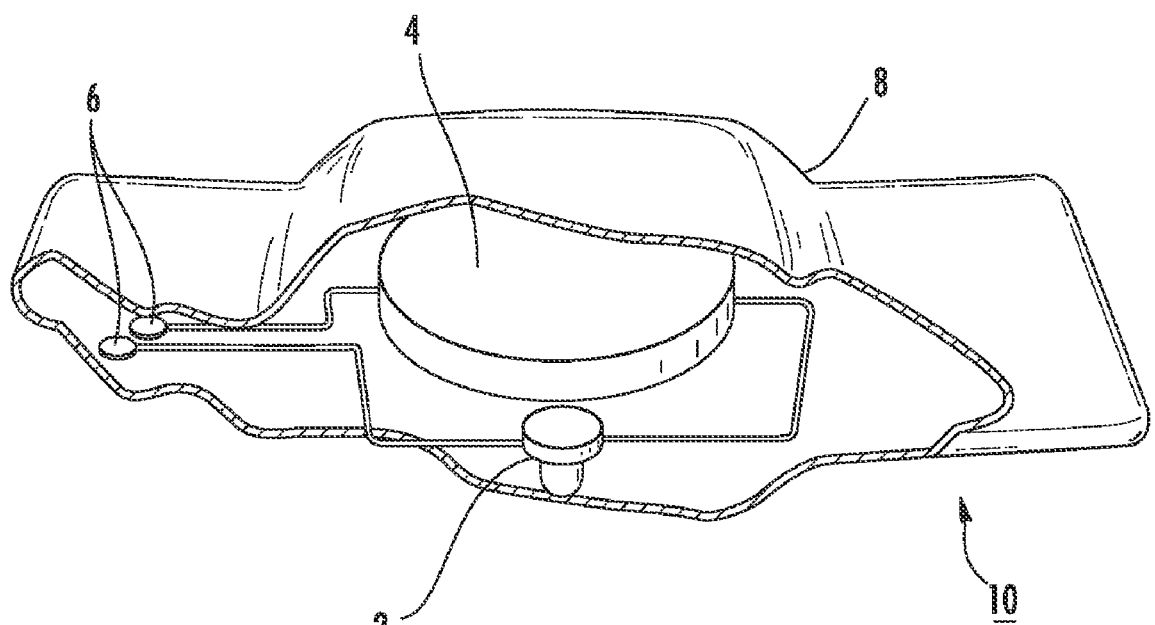
FIG. 1B is a drawing of a perspective view of an embodiment of the light emitting device of the present invention.

Referring to FIGS. 1A and 1B, device 10 includes light emitting diode 2 electronically connected to rechargeable disk battery 4, and a tooth actuated switch 6. Light emitting diode 2, disk battery 4 and switch 6 are encapsulated by housing 8. The housing is adapted or shaped to fit in a user's mouth.

Light emitting diode 2 is positioned, when in use, so that the diode is opposite the tongue. One or more light sources can be used and they can be positioned so that light will be directed to the desired area. As further described herein, one or more light sources can be positioned so that the light is directed to any target area of the oral cavity. Target surfaces include one or more teeth, and a surfaces of the cheek, gum and tongue or combinations thereof. Surfaces of these target areas include palatal surfaces, buccal surfaces, lingual surfaces, facial surfaces, and any combination thereof. The light emitters can target areas as desired. For example, a patient or dentist who wants to alleviate bacteria on the tongue can choose a device with light emitting diodes directed to surfaces of the tongue. However, a patient wanting to whiten teeth can choose a device with light emitters directed to facial surfaces of teeth, and a patient with periodontitis can utilize one with diodes that direct light to the gums and gum pockets. Alternatively, the device of the present invention can have light emitting diodes that direct light to all of these areas. In yet another embodiment, the device includes light sources whose position can be adjusted depending on the area that the user wants to target. The light source can be angled to direct light to the desired target area. For example, a device having light emitting diodes directed to teeth can be repositioned to be directed toward the gum line.

The number of light emitting diodes vary and depend on the areas targeted, the amount of light to be administered, the frequency of the light, the shape of the light emitting diode, and the result to be conferred. The number of light emitters range from about 1 to about 12 light emitting diodes. Light emitting diode 2 is a rounded shaped diode directed to the top surface of the tongue. The light source can be elongated or shaped to complement the target area/surface. For example, to target the buccal surface of a series of teeth, an elongated light source can be used and directed along the length of several teeth.

A light source refers to a source that provides light to reduce the number of bacteria in the mouth, whitens teeth and/or otherwise improves oral health. In an embodiment, the light sources includes sources that emit light at a wavelength ranging from about 350 nm to about 700 nm, and/or a power density that ranges from about 1 mW/cm$^2$ to about 1000 mW/cm$^2$.

In addition to Light Emitting Diodes (LED), light sources of the present invention also include e.g., fiber optic channels, light pipes, gas plasma, linear flash lamps, tungsten halogen, metal halide, Xenon short arc, Mercury short arc, Mercury Xenon short arc, Argon plasma arc, and Argon short arc lamps. The light energy can also be provided by an array of light emitting diodes or laser diodes of suitable wavelength and sufficient power. The light energy can also be provided by chemiluminescent or electroluminescent means. Other light sources are described in U.S. Pat. No. 6,416,319 and PCT WO 01/26576.

In FIGS. 1A and 1B, device 10 further includes a rechargeable disk battery. Any self contained power source can be used with the present invention. A power source is a source of electricity used to provide power to one or more light sources. One or more power sources (e.g., two, three, four, five or six batteries) can be used, and they can be rechargeable or non-rechargeable. Rechargeable refers to a battery whose electrical energy can be restored, either fully or partially, to a charged state by passing an electrical current in the opposite direction through the cell. In the case of a rechargeable battery, when the device is not in use, the battery of the device can be put into communication with an electrical current, in the proper direction to be recharged. This can be accomplished by using a base, plug, or adaptor that is attached to the device and then plugged into an electrical outlet. The device can be adapted to receive the base, plug, or adaptor. For example, the device can include contacts or prongs, which when set into a base, receives an electrical current that recharges the battery. Alternatively, the device can have an opening to receive a plug that provides an electrical current. Such an opening can be covered when the device is being used in the oral cavity. Yet another embodiment includes a removable battery that can either be replaced and/or recharged in a battery charging device. Methods, devices and adaptations for recharging batteries are known in the art and can be used with the present invention to recharge one or more batteries used in the device.

Figure 5:
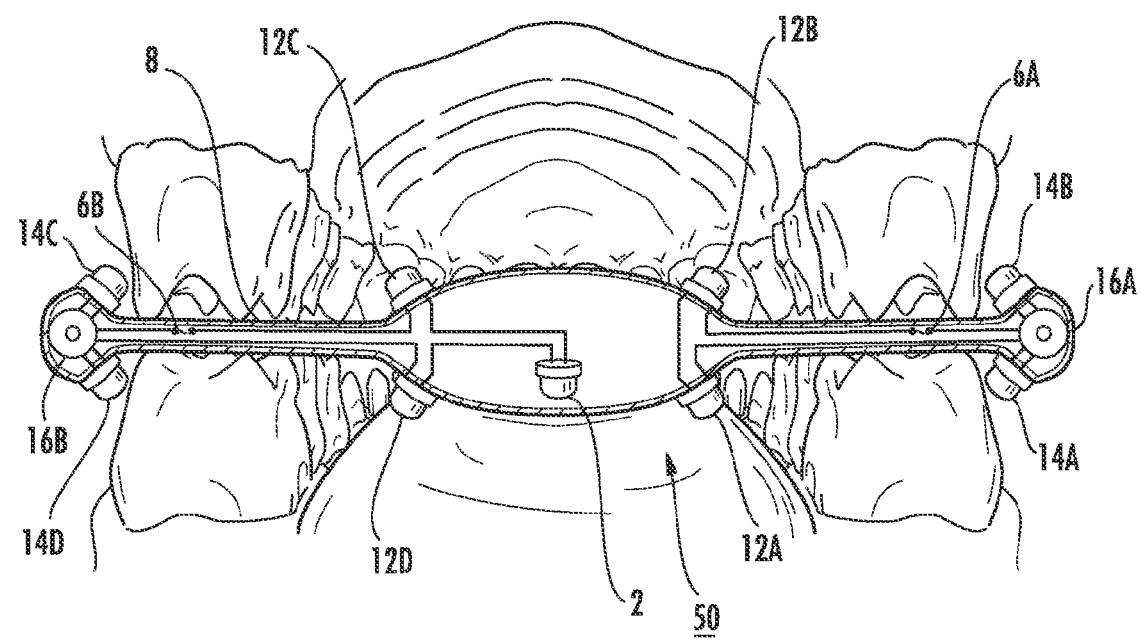
FIG. 5 is a drawing of a side view of yet another embodiment of the light emitting device of the present invention positioned in an oral cavity, wherein the device has batteries in the buccal pockets of the bitewings.

The power source is encapsulated within the device so that the user can fit the device within the oral cavity. In FIGS. 1A and 1B, a disk-like battery or watch battery is used. The present invention includes the use of any self contained power source that can be encapsulated in the device which fits in an oral cavity. A "self contained power source" refers to a power source that has sufficient power to run the device during use (e.g., for at least a single or routine use) without the need of an external power source. Self contained power sources can be recharged when not in use. Examples of batteries that can be used by the present invention include those used for watches and hearing aids (e.g., Zinc Silver Oxide, Lithium ion). Other examples of specific types of batteries include Alkaline batteries, Nickel-iron, Lead, Gel, Absorbed glass mat, Nickel-cadmium, Nickel metal hydride, Lithium ion polymer, Sodium-sulfur, Nickel-zinc, Molten salt, Super iron, and Zinc-bromine flow. The battery can have any shape that fits into the device having a pocket, housing or area which can accommodate the size of the battery. In one aspect, the battery can be placed in the middle of the device, as shown in FIGS. 1A and 1B, so when in use, the battery is under the palate of the user. In another aspect, two alkaline batteries are used and when the device is placed in the user's mouth, the batteries are located in the user's cheek area (see FIG. 5). Any battery arrangement can be used so long as the battery resides within the device, which can fit within the user's mouth.

Device 10 includes switch 6, which is positioned within the housing such that when the user bites down on the device, the switch is actuated. In one aspect, the device has one or more bite wings that contain one or more switches. As used herein, a bite wing is a portion or projection of the device that is placed between the upper and lower teeth, such that when the user bites down on the bite wing, the switch is actuated. The bite wing can be placed between the upper and lower posterior teeth, as shown in FIG. 1A, or between the anterior teeth, or any combination thereof. The device of the present invention can have one more bite wings (e.g., two, three, four). The bite wing that actuates the switch can be anywhere in the user's mouth where the upper jaw and lower jaw meet. As such, the present invention embodies switches in various locations of the device.

Accordingly, the shape of the device can vary depending on the areas of the oral cavity to be targeted so long as the device has a self-contained battery and light source, along with a bite actuated switch. The shape can be that shown in FIG. 1A, namely one that has a pocket in the middle and two bitewings. Alternatively, the shape can be that shown in FIG. 5, whose bitewings are adapted to receive two rechargeable batteries. Yet another embodiment includes a horseshoe shaped mouth piece that can have a brush or projections, as described herein.

Switch 6 is electrically connected to rechargeable battery 4 and light emitting diode 2. The switch is an open switch and has two ends, an upper contact and a lower contact. The switch remains open until the contacts are connected when the user bites down on device 10 and the electrical circuit is completed. The electricity runs from the battery, through the switch and the light source, and back to the battery to complete the circuit. The contact material can be any conductive material known in the art, or developed in the future. The number of switches and/or contacts can vary and can be arranged in any manner to allow a completion of the electrical circuit. Switch 6 is used to turn light emitting diode 2 on and off. However, a number of switches can be used to turn on and off any number of light sources. For example, a switch can be used to turn on only light sources that emit light on buccal surfaces, or only the lingual surfaces. Switches can be used together with other settings or controls to direct which light sources get turned on during actuation (e.g., while biting down on the device). Various arrangements with settings, controls and switches can be used to accommodate a variety of uses that include tooth whitening, improving halitosis, gum treatment, and other uses described further herein. Settings can be used to vary the output of light delivered, or to target different areas of the oral cavity. In an example, a buccal/lingual setting can be used with the device. When the user chooses the buccal setting, the setting causes a piece of non-conducting material to slide between the contacts of the switch that turns on the lingual facing light sources. The non-conducting material or plate prevents an electrical current to pass to the lingual facing light emitters and therefore only allow the buccal emitters to go on. Various such setting/switch arrangements can be used to accommodate multiple uses for a single device.

Any type of switch can be used to complete the circuit so long as the switch can be activated by the user and the switch can fit within the encapsulated device, which in turn, has a size or shape adapted to fit within the user's mouth. Types of switches include those known in the art and those developed in the future. More than one switch and/or arrangement of switches can be used. For example, a switch on both sides of the device can be used, positioned on both the left and right side of the user's posterior teeth. Accordingly, when the user bites down, both switches are actuated and turn on the light source.

The material used for the contacts of the switch, and for providing electrical communication (e.g., wires, bands, plates) between the parts of the device, can be chosen based on the material's properties including its ability to resist corrosion, electrical conductivity, mechanical strength, cost and toxicity, and the like. Switches, the power source and the light sources can be used in conjunction with other electrical components including resistors, capacitors, circuit boards, heat sinks, light distributors, light pipes, insulators, and others known in the art.

Housing 8 of device 10 is shaped to have a pocket for containing battery 4 and light emitting diode 2, and two bite wings, one containing switch 6. In an embodiment, the housing encapsulates the light source, power source and bite-actuated switch. In another embodiment, the housing encapsulates the power source and the bite-actuated switch, and the light source is disposed on the housing. In both cases, the device and/or the housing is adapted so that a user can receive the entire device in the oral cavity. The device can have one or more bite wings that can be adapted or shaped to receive one or more switches, as described herein.

In the embodiment shown in FIG. 1A, the housing allows for a one piece design. The housing can be made up of one or more pieces. The housing includes material with some flexibility so that when the user bites down on the device, the switch is activated. However, the housing is stiff enough to maintain its shape. The housing can also be a two piece device in which the top and bottom portions fit together. The top and bottom portions can include a track in which the pieces can slide up and down during actuation. In which case, the top and bottom portions can be made of a stiffer material that maintains its shape. Materials used for the housing can be made of flexible or relatively non-flexible material, or a combination thereof, and can be made from a single piece or more than one piece. Materials that can be used for the housing are preferably non-toxic or inert material, and examples include plastic, rubber, and other materials known in the art or developed in the future. In an embodiment, the device is preferably water or liquid proof. The housing and any outer portion of the device be made of a liquid resistant or liquid proof material. Liquid resistant or liquid proof refers to material that resists or prevent liquid from penetrating through the material under conditions normally found in the oral cavity.

In a certain embodiment of the present invention, either external (e.g., reflects from a material with a higher refractive index such as aluminum or silver), or internal reflections (e.g., reflections from where the light originates and reflects off of a material with a lower refractive index such as air, vacuum, or water) can be used to tunnel the light to the target area of the oral cavity, and more particularly, the buccal and/or lingual gum tissues.

A light distributor includes any component that distributes light from a light source to the oral cavity, including but not limited to light pipes (which distribute light through internal reflections) and light guides (which distribute light through external reflections). An embodiment of the device includes one or more light distributors. As the surface area of the oral cavity to be treated increases, for example, the number of light pipes or light guides can also increase. A light distributor can be made from any suitable transmitting material with a high index of refraction, such as a polycarbonate or polymethyl methylacrylate ("PMMA").

In embodiments in which the light source is located within the housing, the housing can further include portions that allow for light to pass through. The housing can include transparent or light passing windows, plates, light distributors, or openings to allow, enhance, or direct light to the target areas of the oral cavity. FIG. 1A shows light emitting diode 2, that emits light through concave window 18. Such a window, in certain embodiments, form a portion of or is integrated into the overall housing of the device. Concave window 18 allows the light to be directed or reflected to a greater surface area of the tongue. The window, in an embodiment, can be faceted to provide certain angles so that light distributed to certain areas of the oral cavity. Such windows can be shaped to reflect light in multiple directions to maximize the surface area that is being treated. As such, a window can be concave, polygonal, or otherwise shaped to reflect light in more than one direction.

Figure 2:
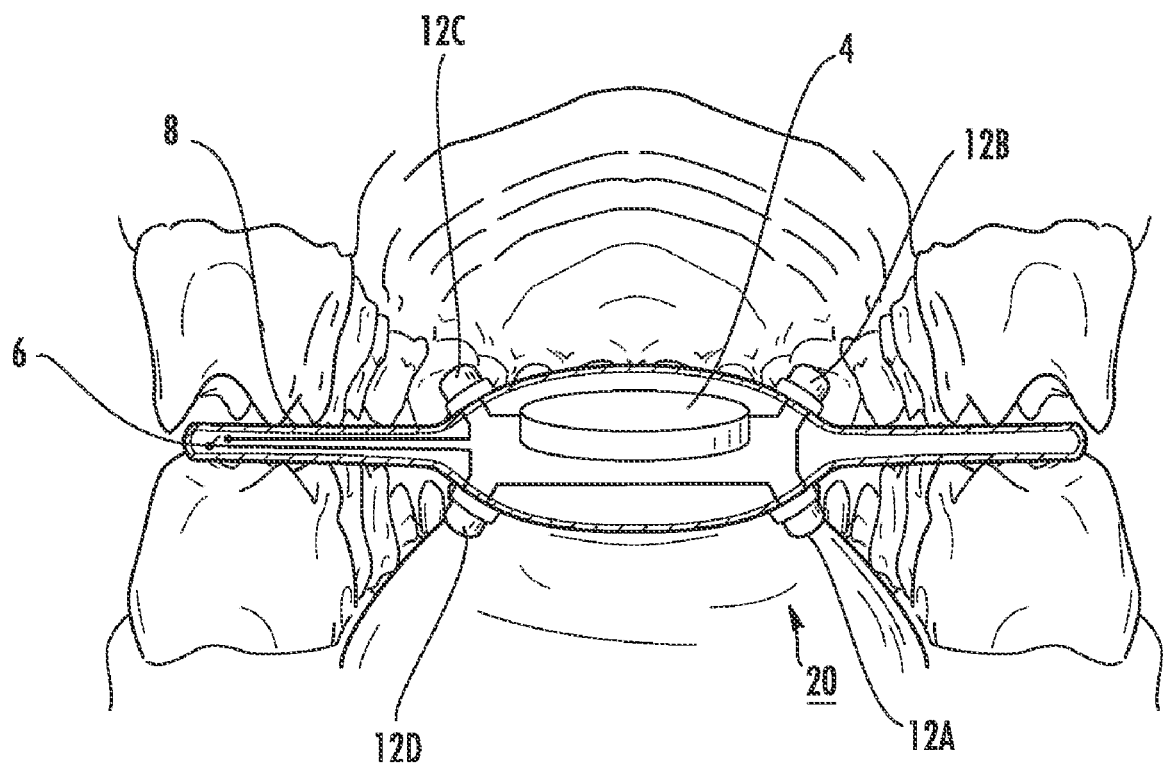
FIG. 2 is a drawing of a side view of another embodiment of the light emitting device of the present invention positioned in an oral cavity, wherein the device emits light to the palatal and lingual surfaces.

Alternatively, light sources can be mounted or disposed on the housing. As shown in FIG. 2, light emitting diodes 12A-D are mounted on housing 8 so that the light is directed to the upper and lower surfaces of the oral cavity. Light emitting diodes 12A-D are mounted at an angle. In an embodiment, diodes or light sources mounted on the housing have a protective cover, or coating to protect any heat build-up in the light source from transferring to the oral cavity. In yet another embodiment, the light source can emit light through a tongue brush or mouthpiece. Such a brush can have a series or plurality of protrusions or projections. Light can be emitted from each projection or between the projections. The brush, in an aspect, can be used to manually remove bacteria and particles from the tongue while simultaneously reducing the bacteria with the light emission. The projections can be optical fibers that carry light and emit it from the tip or any portion thereof. Upon application to the oral cavity, light is delivered to the buccal and lingual sides of the gums.

Also, heat sinks can be used to reduce or control the heat to the light source. A heat sink refers to a device that absorbs and/or dissipates heat from another object using thermal contact (either direct or radiant). A cooling element can be used to reduce or maintain the temperature within the device. The device can also include a thermal sensor which turns off the light source when a certain temperature is reached. Heat sinks, thermal sensors, and similar electrical elements are known in the art and can be used in the device.

The device can optionally further include a timer that causes the light to turn off once a certain time is reached. The timer can be used to time each light session, and/or measure time between sessions. As such, timers can be used to control the amount of light therapy delivered and to avoid overexposure. Timers can be mechanical, electrical, or digital timers or any combination thereof, and integrated into the device. An example of an electrical timer that can be used with the present invention includes a thermal expansion timer. Using a thermal expansion timer, electrical current passes through a finger made of two types of metal. Heat causes the finger to expand on one side faster than the other, and as the finger moves away from a contact, the device can turn off. Any timer known in the art or developed in the future can be used with the present invention.

The device can further include one or more channels or storage areas for solutions or gels that aid in the use of the device. Such storage areas can be used to store mouthwash, solutions that assist in whitening teeth, and/or solutions that assist light in killing or reducing the number of bacterial. Such storage areas can be refillable or replaced with cartridges. Such storage areas or channels, in an embodiment, are positioned such when the user bites down the solution or gel is released mechanically through one or more openings. For example, the bite wing in FIG. 1A that does not contain the switch in device 10 can be adapted to have a channel filled with mouthwash. When the user bites down on the device, the light is turned on and the mouthwash is released. In another embodiment, the solution or gel can be release periodically or continuously during use of the device e.g., using a timer. Such solutions or gels can be placed in the mouth by the user prior to, during or after use of the device of the present invention. Types of solutions that can be used with the device include solutions that kill bacteria and/or freshen breath and examples are chlorine dioxide, chlorhexidine, triclosin. Other solutions that kill bacteria include photosensitizers (e.g., methylene blue, acridine orange), which when come in contact with light further kill or decrease the number of bacteria and freshen breath. A example of a whitening solution includes hydrogen peroxide.

Referring to FIG. 2, device 20 has four light emitting diodes, diodes 12A-D mounted on the housing. Device 20 also has housing 8 with two bite wings, battery 4 and switch 6. The electrical communication is arranged differently to accommodate the additional diodes and complete the circuit via the switch. In this case, device 20 directs light to the lingual surfaces of teeth and/or gum tissue. This device is useful, for example in the treatment of gums and precancerous legions. However, as described herein, the light sources can have any arrangement and be directed to one or more portions of the oral cavity. They can be mounted at an angle, or flush on the housing. The light sources can also be positioned within the housing and optionally used with a window, opening or plate to allow for the passage of light.

Figure 3:
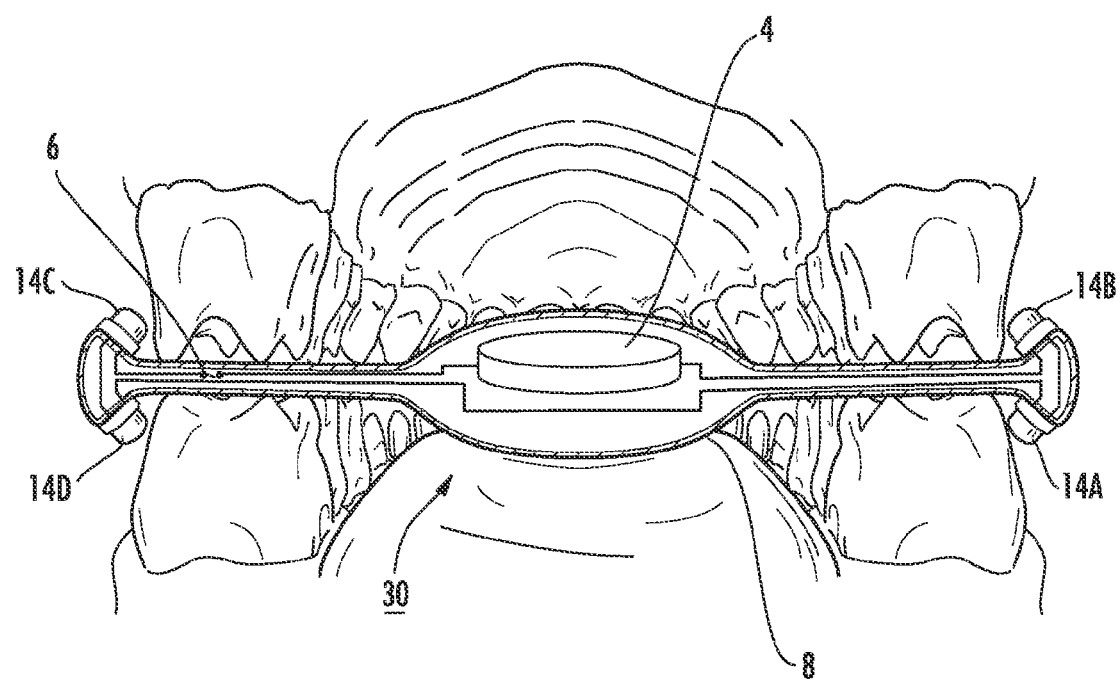
FIG. 3 is a drawing of a side view of another embodiment of the light emitting device of the present invention positioned in an oral cavity, wherein the device emits light to buccal surfaces.

Device 30 of FIG. 3 has light emitting diodes 14A-D on the outermost portions of the bite wings of the device. These light emitting diodes are directed to the buccal surfaces of the oral cavity. Such a device can be used for whitening the outer surfaces of teeth, e.g., particular to the anterior surfaces of the teeth or to treat gum disease.

Figure 4:
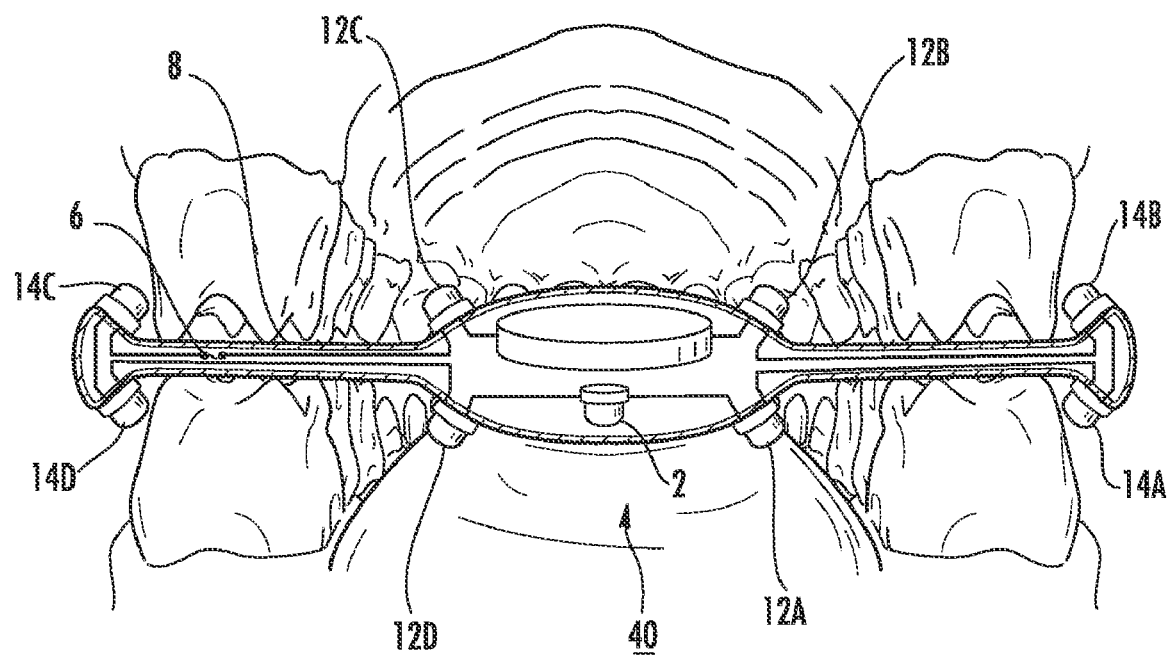
FIG. 4 is a drawing of a side view of yet another embodiment of the light emitting device of the present invention positioned in an oral cavity, wherein the device emits light to buccal, palatal and lingual surfaces.

FIG. 4 shows device 40 having a number of light emitting diodes, 2, 12A-D and 14A-D. In this design, light is directed to the buccal and lingual surfaces of teeth or gum tissue as well as the tongue. Since the light is emitted on several surfaces, this device, in an embodiment, can be useful for lowering overall bacterial counts. Reducing the number of bacterial is associated with improved or freshened breath, and ameliorate certain systemic diseases associated with oral bacteria (e.g., black pigmented bacteria which have been implicated as contributing to cardiovascular disease). The device can be a multi-purpose device, and can be also used one or a combination of the following: whiten teeth, improve halitosis, treat systemic or oral diseases associated with oral bacteria.

Device 50 has the light emitting diodes from the device shown in FIG. 4, but utilizes another type of battery that is positioned differently. In this case, batteries 16A-B are AAA rechargeable alkaline batteries positioned in the outermost portions of the bite wings of the device. The batteries, when the device is in use, reside in the cheek/buccal pocket of the user. The design also uses larger or more powerful batteries, as compared to FIG. 4, to provide a longer duration of illumination at higher intensities. As described for FIG. 4, this device can be used to reduce the number of bacteria to improve halitosis, to whiten teeth, treat gum disease, and prevent or treat certain systemic disease associated with oral bacteria.

The present invention includes methods of administering light to the oral cavity of an individual using a device described herein. The administration of light, as demonstrated in the Exemplification, can be used to reduce the overall number of one or more bacteria in the oral cavity. In addition to reducing the overall bacteria count, the methods of the present invention embody improving halitosis, whitening teeth, improving a gum condition (e.g., gingivitis or periodontitis), treating precancerous lesions or oral cancer, systemic diseases associated with oral conditions such as heart disease, diabetes, and low birth-weight babies, improving overall oral health or any combination thereof. The methods involve applying light or administering light using the device of the present invention, as described herein. In particular, using the device, light is emitted to the oral cavity in a wavelength that ranges from about 350 nm to about 700 nm. In a preferred embodiment, the output is filtered to provide an efficient source of visible blue light in the 380-520 nm range. In one embodiment, light is filtered to be in the 400-505 nm range, or about 475 nm in one embodiment. In another embodiment, the light source is an LED emitting blue light in the range of about 430 nm to about 510 nm, the peak being either about 455 nm or about 470 nm (blue light). In another embodiment, the light source is a gas plasma arc emitting visible light in the range of about 380 nm to about 520 nm visible light. In one embodiment, the light from the light source is not filtered. In another embodiment, the wavelength is about 455 nm. In one embodiment, the wavelength is 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, or 520 nm.

The intensity (energy density) of the light provided by the device of the present invention can range from about 1 $mW/cm^2$ to about 1000 $mW/cm^2$ or higher, or about 1 $mW/cm^2$ to about 800 $mW/cm^2$, or from about 1 $mW/cm^2$ to about 200 $mW/cm^2$, or from about 1 $mW/cm^2$ to about 120 $mW/cm^2$, or about 20 $mW/cm^2$. In another embodiment, the power density, or energy delivered to the teeth, is adjusted to a setting of between about 100 $mW/cm^2$ to about 160 $mW/cm^2$, or, from about 130 $mW/cm^2$ to about 150 $mW/cm^2$.

"Administering" light refers to providing an amount of light to a portion of the oral cavity. An "effective amount" or "therapeutically effective amount" refers to the amount of light and, optionally, agent or action which treats or prevents, in whole or in part, one or more symptoms associated with an oral disease or condition. In particular, the amount of light administered is one that treats or ameliorates one or more oral health symptom, including, but not limited to providing, an anti-inflammatory effect, an anti-bacterial effect, a sterilizing effect, a pain-relieving effect, an increased immune response effect, and a periodontal improvement effect. The therapeutically effective amount of light can be used for prevention and/or treatment purposes. In an embodiment, the therapeutically effective amount of light is at the predetermined wavelength as described herein. Additionally, therapeutically effective amounts of light can be administered in a predetermined dosage. The predetermined dosage can range from about 0.1 $Joules/cm^2$ to about 1000 $Joules/cm^2$, or from about 0.1 $Joules/cm^2$ to about 500 $Joules/cm^2$, or, from about 0.1 $Joules/cm^2$ to about 100 $Joules/cm^2$, or, from about 0.1 $Joules/cm^2$ to about 50 $Joules/cm^2$, or, from about 0.1 $Joules/cm^2$ to about 10 $Joules/cm^2$. In one embodiment, the dosage is from about 0.2 $Joules/cm^2$ to about 1.2 $Joules/cm^2$. In another embodiment, the dosage is about 4.2 $Joules/cm^2$. In still another embodiment, the dosage is about 21 $Joules/cm^2$. In yet another embodiment, the dosage is 2 $Joules/cm^2$, 3 $Joules/cm^2$, 4 $Joules/cm^2$, 5 $Joules/cm^2$, 6 $Joules/cm^2$, 7 $Joules/cm^2$, 8 $Joules/cm^2$, 9 $Joules/cm^2$, 10 $Joules/cm^2$, 11 $Joules/cm^2$, 12 $Joules/cm^2$, 13 $Joules/cm^2$, 14 $Joules/cm^2$, 15 $Joules/cm^2$, 16 $Joules/cm^2$, 17 $Joules/cm^2$, 18 $Joules/cm^2$, 19 $Joules/cm^2$, 20 $Joules/cm^2$, 21 $Joules/cm^2$, 22 $Joules/cm^2$, 23 $Joules/cm^2$, 24 $Joules/cm^2$, 25 $Joules/cm^2$, 26 $Joules/cm^2$, 27 $Joules/cm^2$, 28 $Joules/cm^2$, 29 $Joules/cm^2$, 30 $Joules/cm^2$, 31 $Joules/cm^2$, 32 $Joules/cm^2$, 33 $Joules/cm^2$, 34 $Joules/cm^2$, 35 $Joules/cm^2$, 36 $Joules/cm^2$, 37 $Joules/cm^2$, 38 $Joules/cm^2$, 39 $Joules/cm^2$, 40 $Joules/cm^2$, 41 $Joules/cm^2$, 42 $Joules/cm^2$, 43 $Joules/cm^2$, 44 $Joules/cm^2$, 45 $Joules/cm^2$, 46 $Joules/cm^2$, 47 $Joules/cm^2$, 48 $Joules/cm^2$, 49 $Joules/cm^2$, or 50 $Joules/cm^2$.

"Treating" refers to improving or making better one or more symptoms associated with the disease or condition, as compared to the state of the symptom prior to treatment, or as compared to a control. "Improving oral health" refers to ameliorating one or more symptoms associated with oral diseases or conditions. Examples of such symptoms include bad breath, increased overall count of one or more bacteria, discolored teeth or non-whitened teeth, gum bleeding, gum swelling, inflammation, lesions (e.g., cancerous and pre-cancerous), pain, decay, sensitivity, and slow healing. Symptoms of oral diseases or conditions are known in the art and recognized by a dentist.

The duration of exposure of the light to the teeth and/or gums can range from about 5 seconds to about an hour, or about 5 seconds to about 15 minutes, or about 5 seconds to about five minutes, or about 5 seconds to about two minutes, or from about 5 seconds to one minute. The duration of exposure can be specifically 5 seconds, 10 seconds, 15 seconds, 30 seconds, 45 seconds, one minute, two minutes, three minutes, four minutes, five minutes, 10 minutes, 15 minutes, 20 minutes, 30 minutes, 40 minutes, 50 minutes, or one hour. The light source can automatically turn off after the duration of application. As higher light intensity is reached, the duration of exposure can decrease. In one embodiment, the device 10 is placed in the oral cavity for about 2 minutes.

The frequency of application of light to the oral cavity can be on a periodic basis (e.g., daily, weekly, monthly, or annual basis). When the method of the present invention is performed at home by the subject, the subject exposes the light source to the oral cavity for the selected time period for about 1, 2, 3, 4, 5, or 6 times every day, week, month, or year for the selected period of time. For example, the period can range from about two weeks to about one month, six months, nine months, or one year. When the method of the present invention is performed in a dental office, the method can be performed by a dental professional at least 1, 2, 3, 4, or 5 times a year in less than about 1 hour (e.g., less than about 30 minutes, 20 minutes, 10 minutes, or 5 minutes). The application of light can be intermittent, pulsed, or continuous with each application.

Light can be administered continuously, intermittently, or combinations thereof, over a period of time. In an embodiment, the light is administered by the device for a period of between about 1 to about 3 minutes, once or twice a day, or as needed throughout the day. In another aspect, the light is emitted in the oral cavity for a periodic interval (e.g., about 20, 30, 40, or 50 second intervals), and then repeated one, two or three times. The amount of light, the interval of light administration (e.g., between about 10 seconds to about 3 minutes), and the number of times in a day (e.g., between about 1 to about 2 times a day), week (e.g. between about 1 to about 14 times a week), or month (e.g., between about 1 to about 62 times a month) light is administered can vary and will depend on the desired effect, whether an agent (e.g., solution or gel) is being used to increase the efficacy of the light treatment, and the condition being treated.

In particular, one or more of the following variables relating to the light exposure are encompassed by the present invention, (1) the type of light source used; (2) the intensity/irradiance of the light; (3) the wavelength of the light emitted from the light source; (4) the duration of the exposure of the light to the teeth and gums; and (5) the frequency of application. The variables, in certain aspects, depend on another. For example, an increase in the duration of exposure can decrease the intensity of the light emitted.

As described herein, methods of the present invention relate to reducing the number of one or more bacteria in the oral cavity by providing or administering light using the device described herein. This is performed, in one aspect, by administering light at the wavelength and power, also as described herein. Administration occurs by inserting the device in the oral cavity, and then biting down on it to turn the device on. An agent that assists in eliminated bacteria can be also administered before, during or after treatment. Examples of such agents are chlorine dioxide, chlorhexidine, triclosin, chelators, cleaning agents, and oxidizing agents, which can be used to assist in eliminating bacteria, whitening teeth, or both.

Oxidizing agents include, but are not limited to, hydrogen peroxide (and any hydrogen peroxide precursor), carbamide peroxide, calcium carbonate peroxide, sodium carbonate peroxide, sodium percarbonate, calcium peroxide, sodium perborate, potassium persulfate, peracetic acid (and other peracids), chlorine dioxide, and other oxygen radical generating agents. In one embodiment, the oxidizing agent composition comprises from about 5.0% (w/w) to about 35.0% (w/w) hydrogen peroxide. Other oxidizing agent compositions comprise from about 3.0% (w/w) to about 20.0% (w/w) hydrogen peroxide. Other oxidizing agent compositions comprise from about 6.0% (w/w) to about 15.0% (w/w) hydrogen peroxide.

Calcium and iron chelators can also be used by itself or in combination with the oxidizing agent to eliminate or reduce bacteria in the oral cavity, or to make the bacteria more susceptible to killing by light. Suitable chelating agents include but are not limited to EDTA and its salts, citric acid and its salts, gluconic acid and its salts, etidronic acid (Dequest 2010), alkali metal pyrophosphates, iron chelating agents and other compounds capable of sequestering or chelating iron, and alkali metal polyphosphates. Alternatively, a composition comprising an iron chelator can be used alone or in combination with an oxidizing agent to increase the susceptibility of oral bacteria to light.

In yet another aspect of the present invention, a cleaning agent is administered to the oral cavity of the subject prior to, during or after administration of light to the oral cavity of the subject. The cleaning agents can be mechanical (such as an abrasive) or chemical in mode of action. Such cleaning agents can include but are not limited to toothpastes, mouthwashes, and active agents delivered from floss.

To determine if the number of bacteria is reduced, a sample from the oral cavity can be obtained. Bacteria can be grown, cultured or tested to determine which bacteria exists and their overall number. Alternatively, the nucleic acid of the bacteria of the sample can be assayed using gene chip technology or nucleic acid hybridization techniques. Methods of determining the types and number of bacteria that exist in a sample are known in the art. After treatment or light administration occurs using the device of the present invention, and another sample can be obtained. The results from the two samples are compared, and a reduction of the number of one or more bacteria occurs. In another embodiment, bacteria levels after treatment can be compared to a control (e.g., the average levels of bacteria in a similar patient population or pool) to determine that bacteria levels have been reduced. In an embodiment, the methods described herein reduces or eliminates from about 5% to about 25%, about 5% to about 50%, about 5% to about 75%, or about 5% to about 100% of one or more bacteria present in the oral cavity. In another embodiment, from about 5% to about 25%, about 5% to about 50%, about 5% to about 75%, or about 5% to about 100% of black-pigmented bacteria in the oral cavity is reduced after exposure to light. The reduction of certain bacterial also improve the overall oral health and halitosis. Similarly, a reduction in the number of bacteria prevents or treats symptoms of systemic disease associated with oral conditions such as heart disease, diabetes, and low birth-weight babies.

As such, a reduction in the odor or halitosis from the oral cavity is an indication that a reduction in the number of one or more bacteria has occurred. Methods for improving halitosis include administering light, as described herein, and optionally applying one or more agents. A reduction in bad breath or odor can be determine by observation of the person whose oral cavity is being treated, as compared to the state of halitosis prior to treatment or to a control (e.g., average levels of halitosis in a similar patient population).

Furthermore, the present invention relates to whitening teeth. Teeth have been whitened by application of an external light and a peroxide gel. As such, the methods include applying a tooth whitening agent (e.g., a peroxide gel or oxidizing agent as described herein), and administering light using the light emitting device of the present invention at a wavelength, power, and time interval, also as described herein. Application of light by the device with a tooth whitening agent results in an increase the whiteness of one or more teeth (e.g., as measured using a standard shade guide such as A-D, 1-4), and/or reduces discoloration of one or more teeth.

Similarly, methods of the present invention include improving a user's gum condition (e.g., gingivitis or periodontitis). Accordingly, the present invention includes administration of light to improve one or more symptoms associated with the gum conditions. For example, gingivitis is a soft tissue gum condition whose symptoms include the bleeding of gums and gum swelling. After light administration at wavelengths, power, and time intervals described herein one or more of these symptoms are decreased. Similarly, periodontitis, in addition to gum bleeding and gum swelling, symptoms further includes the formation of periopockets, pockets between the gum and teeth. As such, light administration, in an embodiment, decreases size of these pockets, along with decreasing gum bleeding and/or gum swelling.

With respect to treating cancer or a precancerous lesion, administration of light with the device, as described herein, results in decreasing the size, severity, amount of cancer cells or precancerous lesion. Cancer or precancerous lesions in the oral cavity are often characterized by discoloration (e.g., darker, white, or red), and/or irregular shape. A biopsy of the cancer cells or precancerous lesions can be performed to determine the extent and severity of the condition. In certain embodiments, administration of light, as described herein, along with e.g., a photosensitizing compound results in a decrease of the size, severity and/or amount of cells that are cancerous or pre-cancerous.

Certain agents used in the methods of the present invention are agents that improve oral health by enhancing or assisting in the effect of light therapy administered as described herein. Agents are referred to herein as a compound that enhances or increases the effect of the light therapy. Agents can be administered as gels, solutions, or in strips (e.g., a whitening strip). Any combination of agents along with the device can be used to carry out the methods of the present invention. For example, a tooth whitening agent is an agent that enhances the tooth whitening effect. A photosensitizer or oxidizing agent can increase the number of bacteria being killed when used with the light device of the present invention. Additionally, cleaning agents such as mouthwash can be used to further reduce the overall bacteria number, but also freshen breath (e.g., reduce halitosis). As such, the methods of the present invention include administering or applying one or more agents prior to, during or after administration of light therapy. Example of such agents include chlorine dioxide, chlorhexidine, triclosin, oxidizing agents, photosensitizers, calcium and/or iron chelators and cleaning agents.

The agents are administered by applying the agent to one or more portions of the oral cavity. The actual effective amounts of an agent can vary according to the specific agent being utilized, the particular composition formulated, and the condition of the patient, for example. As used herein, an effective amount of an agent is an amount that can reduce or make better one or more symptoms associated with an oral disease or condition. Dosages for agents are known in the art or can be determined using methods and protocols known in the art, such as conventional pharmacological protocol.

Light in combination with one or more agents can be administered. Administration of agents is optional. When administering light and one or more agents, the administration can occur simultaneously or sequentially in time. The agent and light can be administered before and after one another, or at the same time. Thus, the term "co-administration" is used herein to mean that the agent and light will be administered at times to improve oral health or reduce the occurrence, severity of one or more symptoms associated with oral disease or condition, as described herein. The methods of the present invention are not limited to the sequence in which the light and/or one or more agents are administered, so long as they are administered close enough in time to produce the desired effect. The methods also include co-administration with other drugs that used to treat oral diseases or conditions.

The device of the present invention embodies at home use by the patients. Other embodiments include utilization of the devices of the present invention by dental professionals during in-office procedures, or in regimens using a combination of in-office and home device use.

The present invention further includes systems and kits for improving oral health. Such systems and kits include the device described herein, and an item or agent associated with improving oral health or using the device. Agents include those that enhance the effect of the light therapy administered by the device, as described herein. Such items associated with using the device include batteries and/or a device, plug or adapted to charge the battery. Items associated with oral heath include toothbrushes, sonic brushes, mouthwash, floss, tongue scrapers, and the like.

EXEMPLIFICATION

Oral Disease Conditions Amenable to Light Therapy

Figure 6:
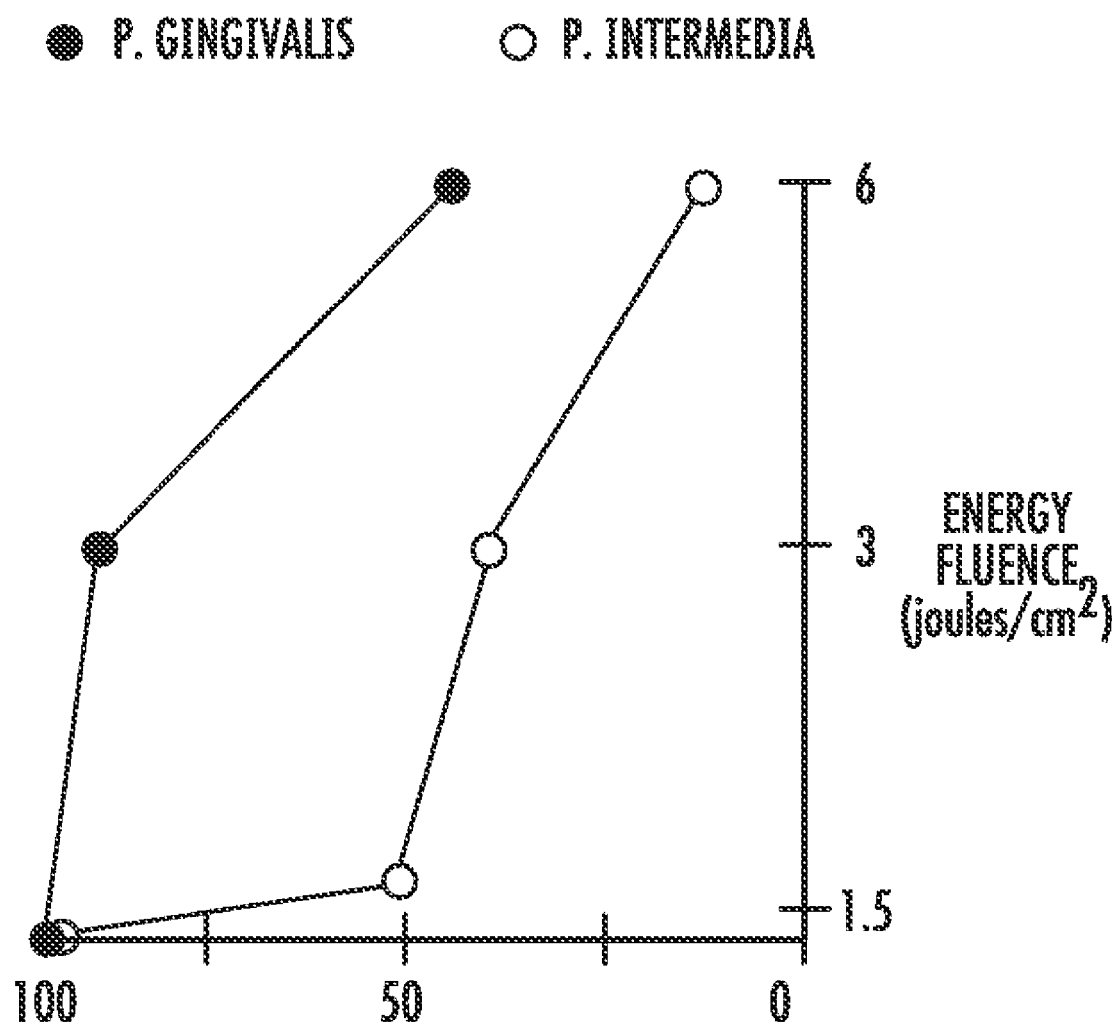
FIG. 6 is a graphical representation of the bacterial count of *P. Gingivalis* or *P. Intermedia* as compared with energy fluence (joules/cm$^2$).

Antibacterial effects: Representative studies on pure bacterial cultures of the periodontal disease pathogens *P. gingivalis* and *P. intermedia* showed that when they were exposed to blue light with a peak at 455 nm and a spectral range from 430 to 480 nm light these species were killed (see FIG. 6). In this case, the irradiation source was a light-emitting diode. The energy fluences delivered to the wells were 1.5, 3 and 6 J/cm$^2$, which corresponded with 15, 30 and 60 seconds of exposure to light respectively and the power density was 100 mW/cm$^2$. The effects of increasing light doses from the light source on cultures of *P. gingivalis* and *P. intermedia* were to eliminate *P. intermedia* by 95% after exposure to light with fluence of 6 J/cm$^2$ (1 min irradiation). The survival fraction of *P. gingivalis* was 55% after light exposure with the same fluence.

Percentage of *P. gingivalis* and *P. intermedia* survived following exposure to different levels of energy. These observations were linked to bacterial cell content of the black pigment porphyrin. It was also found that these effects of light may be achieved by even shorter duration exposures. An example of this observation is summarized in the following experiment:

Multi-species biofilms were grown on agar in 96-well plates using dental plaque obtained from a patient with chronic destructive periodontitis. Biofilms were divided in 8 groups (4 biofilms per group). Four consecutive illuminations by blue light of 455 nm were given to these biofilms (one exposure every day). The light parameters were: power density=50 mW/cm$^2$ and energy fluence=1 Joule/cm$^2$. The time of exposure was 20 sec each time. After illumination, adherent bacteria were scraped and dispersed in pre-reduced anaerobically sterilized brain heart infusion broth. Cell numbers were measured, serial dilutions were prepared in PRAS media and bacteria were spread over the surfaces of blood agar plates and incubated anaerobically at 37° C. for 7 days. Microbial analysis was performed using DNA-DNA hybridization. Data were expressed as % DNA probe counts. The mean of values was obtained from 4 wells per group.

TABLE 1

Reduction Proportions of Black-Pigmented Bacteria (BPB) by Repetitive Exposure

|  | Day 1 | Day 2 | Day 3 | Day 4 | TOTAL | BPB (%) |
| --- | --- | --- | --- | --- | --- | --- |
| Biofilm 1 | 1 Joule | — | — | — | 1 Joule | 4% |
| Control 1 | 0 Joule | — | — | — | 0 Joule | 4% |
| Biofilm 2 | 1 Joule | 1 Joule | — | — | 2 Joule | 4% |
| Control 2 | 0 Joule | 0 Joule | — | — | 0 Joule | 4% |
| Biofilm 3 | 1 Joule | 1 Joule | 1 Joule | — | 3 Joule | 4.3% |
| Control 3 | 0 Joule | 0 Joule | 0 Joule | — | 0 Joule | 5% |
| Biofilm 4 | 1 Joule | 1 Joule | 1 Joule | 1 Joule | 4 Joule | 5.7% |
| Control 4 | 0 Joule | 0 Joule | 0 Joule | 0 Joule | 0 Joule | 9.3% |

In this biofilm model, the BPB normally increase with time so that the effects of light are seen as the difference between test (1 Joule) and control (0 Joule) with each exposure protocol. No difference in the proportion of BPB species was found in biofilms after two light exposures. At day 3, there was a slight reduction of BPB compared with controls. By day 4, however, the proportion of BPB in test wells was reduced by 40% relative to control wells. These data show that repetitive short exposures to light (in this case 20 seconds) lead to a cumulative suppressive effect on the growth of dental plaque BPB.

Effects on oral malodor (halitosis): A principle component of oral malodor is caused by volatile sulfur compounds (VSC) produced by bacteria in the oral cavity, particularly on the upper surface of the tongue. The major components of VSC in oral malodor are hydrogen sulfide (H2S), methyl mercaptan and dimethyl sulphide. BPB of the tongue have been recognized as potent producers of VSC. High prevalence of *P. intermedia* and *P. gingivalis* were found in halitosis and have a high capability of producing VSC in vitro. Hence exposure of the oral tissue and especially the tongue to light reduces bacteria that produce oral malodor.

Effects on gingivitis: The most common BPB associated with gingivitis are the *Prevotella* species *P. intermedia, P. nigrescens* and *P. melaninogenica*. In our studies of 20 subjects enrolled in an experimental gingivitis study and followed longitudinally by DNA-probe methods, it was observed that *P. nigrescens, P. intermedia* and *P. melaninogenica* proliferated toward the end of the study whereas *P. gingivalis* did not. This proliferation was associated with an increasing tendency to bleed as measured by the blood volume released following 60-gram controlled-force probing. These data suggest that proliferation of *Prevotella* species is responsible for the increased bleeding tendency of long-standing gingivitis. Hence, exposure of the gums affected by gingivitis will reduce signs of gingivitis.

Effects on cardiovascular disease: In periodontitis, there is a shift in the composition of subgingival plaque's microflora that colonizes tooth surfaces and epithelial cells in the periodontal pocket to a more proteolytic Gram-negative anaerobic community including the pigmented rods in the genera *Porphyromonas* and *Prevotella*. Studies suggest that chronic periodontitis is often a risk factor for atherosclerosis and subsequent cardiovascular disease. Direct evidence in the potential pathogenity of *P. gingivalis* and *P. intermedia* is provided by the detection of their DNA in atheroma plaques. Additionally, *P. gingivalis* bacteremia promoted coronary and aortic atherogenesis in pigs with or without significant hypercholesterolemia. The inflammatory marker C-Reactive Protein (CRP) is synthesized and secreted by hepatocytes in response to inflammation. CRP was significantly increased in 109 subjects with moderate to severe periodontitis when compared with 65 periodontally healthy controls (P=0.036). The presence of periodontal pathogens from subgingival plaque samples, including the BPB *P. gingivalis* and *P. intermedia*, was positively associated with elevated CRP levels (P=0.029). CRP levels were also reported to be higher in 50 human subjects with cardiovascular disease, who exhibited severe periodontitis with >4 mm deep pockets, compared with 46 healthy controls. Recently, it has been reported that topical application of 10 mg of minocycline into periodontal pockets in 15 human subjects with chronic periodontitis for one month caused a significant decrease of CRP values from 1.6+1.7 ng/ml to 0.93+1.0 ng/ml (P<0.01). A decrease of serum levels of CRP has also been reported after periodontal treatment (mechanical plaque control, root scaling and planning. Significant reductions of serum CRP in patients with severe generalized periodontitis two months after mechanical removal of plaque and local application of minocycline hydrochloride have been reported. Hence, reduction of oral BPB by light exposure reduce CRP and other measures of cardiovascular disease. Similarly, oral BPB is implicated with increased severity of diabetes.

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. An oral light emitting device for targeting light to surfaces within the oral cavity, wherein the device comprises:
   a. a housing including one or more light sources that emit a wavelength that ranges from about 350 nm to about 700 nm, wherein the one or more light sources having a means for emitting focused light to one or more inner surfaces of the oral cavity, said inner surfaces selected from the group consisting of the tongue, teeth, gums, a lingual surface, a buccal surface, a palatal surface, a facial surface, and any combination thereof, for purposes of improving an oral disease or condition, improving oral health, reducing bacteria, improving halitosis, whitening teeth, improving a gum condition, improving a systemic disease associated with an oral condition, or any combination thereof;
   b. a power source in electrical communication with the light source; and
   c. a bite actuated switch in electrical communication with the power source and the light source, wherein the power source and switch are encapsulated within the housing;

wherein the device is a size that fits within an oral cavity of an individual; and the device emits a power density that ranges from about 1 mW/cm2 to about 200 mW/cm2 and an energy fluence that ranges from about 0.1 Joules/cm2 to about 1000 Joules/cm2.

2. The oral light emitting device of claim 1, wherein the housing is liquid proof.

3. An oral light emitting device for targeting light to surfaces within the oral cavity, wherein the device comprises:
   a. a housing including one or more light sources that emit a wavelength that ranges from about 350 nm to about 700 nm, wherein the one or more light sources having a means for emitting focused light to one or more inner surfaces of the oral cavity, said inner surfaces selected from the group consisting of the tongue, teeth, gums, a lingual surface, a buccal surface, a palatal surface, a facial surface, and any combination thereof, for purposes of improving an oral disease or condition, improving oral health, reducing bacteria, improving halitosis, whitening teeth, improving a gum condition, improving a systemic disease associated with an oral condition, or any combination thereof;
   b. one or more power sources in electrical communication with the light source; and
   c. one or more bite actuated switches in electrical communication with the power source and the light source;

wherein the housing encapsulates the power source and bite actuated switch, the device is shaped or sized to fit within an oral cavity of an individual; and the device emits a power density that ranges from about 1 mW/cm2 to about 200 mW/cm2 and an energy fluence that ranges from about 0.1 Joules/cm2 to about 1000 Joules/cm2.

4. The oral light emitting device of claim 3, further including a bitewing that houses the bite actuated switch.

5. The oral light emitting device of claim 3, further including a timer.

6. A method for providing light to an oral cavity of a user with a light emitting device wherein the device comprises a housing including one or more light sources that emit a wavelength that ranges from about 350 nm to about 700 nm, wherein the one or more light sources having a means for emitting focused light to one or more inner surfaces of the oral cavity, said inner surfaces selected from the group consisting of the tongue, teeth, gums, a lingual surface, a buccal surface, a palatal surface, a facial surface, and any combination thereof, for purposes of improving an oral disease or condition, improving oral health, reducing bacteria, improving halitosis, whitening teeth, improving a gum condition, improving a systemic disease associated with an oral condition, or any combination thereof; a power source in electrical communication with the light source; and a bite actuated switch in electrical communication with the power source and the light source, wherein the power source and switch are encapsulated within the housing; wherein the device is a size that fits within an oral cavity of an individual; and the device emits a power density that ranges from about 1 mW/cm2 to about 200 mW/cm2 and an energy fluence that ranges from about 0.1 Joules/cm2 to about 1000 Joules/cm2; wherein the device is placed within the user's oral cavity, wherein method comprises:

actuating a bite actuated switch, wherein when actuated, the device emits light to the oral cavity.

7. A method for providing light to an oral cavity of a user with a light emitting device wherein the device comprises a housing including one or more light sources that emit a wavelength that ranges from about 350 nm to about 700 nm, wherein the one or more light sources having a means for emitting focused light to one or more inner surfaces of the oral cavity, said inner surfaces selected from the group consisting of the tongue, teeth, gums, a lingual surface, a buccal surface, a palatal surface, a facial surface, and any combination thereof, for purposes of improving an oral disease or condition, improving oral health, reducing bacteria, improving halitosis, whitening teeth, improving a gum condition, improving a systemic disease associated with an oral condition, or any combination thereof; a power source in electrical communication with the light source; and a bite actuated switch in electrical communication with the power source and the light source, wherein the power source and switch are encapsulated within the housing; wherein the device is a size that fits within an oral cavity of an individual; and the device emits a power density that ranges from about 1 mW/cm2 to about 200 mW/cm2 and an energy fluence that ranges from about 0.1 Joules/cm2 to about 1000 Joules/cm2; wherein the method comprises:

a. inserting the device into the user's oral cavity; and b. biting down on the bite actuated switch, wherein when actuated, the device emits light to the oral cavity.

8. A method for improving oral health with a light emitting device wherein the device comprises a housing including one or more light sources that emit a wavelength that ranges from about 350 nm to about 700 nm, wherein the one or more light sources having a means for emitting focused light to one or more inner surfaces of the oral cavity, said inner surfaces selected from the group consisting of the tongue, teeth, gums, a lingual surface, a buccal surface, a palatal surface, a facial surface, and any combination thereof, for purposes of improving an oral disease or condition, improving oral health, reducing bacteria, improving halitosis, whitening teeth, improving a gum condition, improving a systemic disease associated with an oral condition, or any combination thereof; a power source in electrical communication with the light source; and a bite actuated switch in electrical communication with the power source and the light source; wherein the power source and switch are encapsulated within the housing wherein the device is a size that fits within an oral cavity of an individual; and the device emits a power density that ranges from about 1 mW/cm2 to about 200 mW/cm2 and an energy fluence that ranges from about 0.1 Joules/cm2 to about 1000 Joules/cm2; wherein the method comprises:

a. inserting the device into the user's oral cavity;

b. biting down on the bite actuated switch, wherein when actuated, the device emits light to the oral cavity; and c. administering one or more agents to the oral cavity, wherein the agent assists in eliminating bacteria, whitening teeth, improving halitosis, cleaning teeth, tongue or gums, or any combination thereof;

wherein a reduction in one or more of the following occurs: a number of one or more bacteria; more symptoms associated with halitosis; and symptoms associated with one or more gum conditions or diseases.

9. A method for whitening teeth with a light emitting device wherein the device comprises a housing including one or more light sources that emit a wavelength that ranges from about 350 nm to about 700 nm, wherein the one or more light sources having a means for emitting focused light to one or more inner surfaces of the oral cavity, said inner surfaces selected from the group consisting of the tongue, teeth, gums, a lingual surface, a buccal surface, a palatal surface, a facial surface, and any combination thereof, for purposes of improving an oral disease or condition, improving oral health, reducing bacteria, improving halitosis, whitening teeth, improving a gum condition, improving a systemic disease associated with an oral condition, or any combination thereof; a power source in electrical communication with the light source; and a bite actuated switch in electrical communication with the power source and the light source, wherein the power source and switch are encapsulated within the housing; wherein the device is a size that fits within an oral cavity of an individual; and the device emits a power density that ranges from about 1 mW/cm2 to about 200 mW/cm2 and an energy fluence that ranges from about 0.1 Joules/cm2 to about 1000 Joules/cm2; wherein the method comprises:

a. applying at least one tooth whitening agent;

b. inserting the device into the user's oral cavity; and c. biting down on the bite actuated switch, wherein when actuated, the device emits light to the oral cavity;

wherein one or more teeth are whitened.

10. An oral light emitting system, wherein the system comprises:

a. an oral light emitting device, wherein the device comprises:

i. a first housing including one or more light sources that emit a wavelength that ranges from about 350 nm to about 700 nm, wherein the one or more light sources having a means for emitting focused light to one or more inner surfaces of the oral cavity, said inner surfaces selected from the group consisting of the tongue, teeth, gums, a lingual surface, a buccal surface, a palatal surface, a facial surface, and any combination thereof, for purposes of improving an oral disease or condition, improving oral health, reducing bacteria, improving halitosis, whitening teeth, improving a gum condition, improving a systemic disease associated with an oral condition, or any combination thereof;

ii. a second housing for a power source in electrical communication with the light source; and iii. a bite actuated switch in electrical communication with the power source and the light source, wherein the second housing for the power source and switch are encapsulated within the first housing;

wherein the device is a size that fits within an oral cavity of an individual; and b. a power source, wherein when coupled to the power source, the device emits a power density that ranges from about 1 mW/cm2 to about 200 mW/cm2 and an energy fluence that ranges from about 0.1 Joules/cm2 to about 1000 Joules/cm2.

11. The oral light emitting system of claim 10, further including a device that recharges the power source.

12. The oral light emitting system of claim 10, further including an agent that assists in eliminating bacteria, whitening teeth, improving halitosis, cleaning teeth, tongue or gums, or any combination thereof.

13. An oral light emitting kit, wherein the kit comprises:

a. an oral light emitting device, wherein the device comprises:

i. a first housing including one or more light sources that emit a wavelength that ranges from about 350 nm to about 700 nm, wherein the one or more light sources having a means for emitting focused light to one or more inner surfaces of the oral cavity, said inner surfaces selected from the group consisting of the tongue, teeth, gums, a lingual surface, a buccal surface, a palatal surface, a facial surface, and any combination thereof, for purposes of improving an oral disease or condition, improving oral health, reducing bacteria, improving halitosis, whitening teeth, improving a gum condition, improving a systemic disease associated with an oral condition, or any combination thereof;

ii. a second housing for a power source in electrical communication with the light source; and iii. a bite actuated switch in electrical communication with the power source and the light source, wherein the second housing for the power source and switch are encapsulated within the first housing;

wherein the device is a size that fits within an oral cavity of an individual;

b. a power source, wherein when coupled to the power source, the device emits a power density that ranges from about 1 mW/cm2 to about 200 mW/cm2 and an energy fluence that ranges from about 0.1 Joules/cm2 to about 1000 Joules/cm2; and c. one or more agents that assists in eliminating bacteria, whitening teeth, improving halitosis, cleaning teeth, tongue or gums, or any combination thereof.

* * * * *